(12) United States Patent
Dunne

(10) Patent No.: US 8,425,973 B2
(45) Date of Patent: Apr. 23, 2013

(54) THREE-DIMENSIONAL FABRICATION

(75) Inventor: Patrick C. Dunne, Maynard, MA (US)

(73) Assignee: 3M Innovative Properties Company, Saint Paul, MN (US)

( * ) Notice: Subject to any disclaimer, the term of this patent is extended or adjusted under 35 U.S.C. 154(b) by 370 days.

(21) Appl. No.: 12/744,751

(22) PCT Filed: Nov. 26, 2008

(86) PCT No.: PCT/US2008/084792
§ 371 (c)(1),
(2), (4) Date: May 26, 2010

(87) PCT Pub. No.: WO2009/073498
PCT Pub. Date: Jun. 11, 2009

(65) Prior Publication Data
US 2010/0310786 A1 Dec. 9, 2010

Related U.S. Application Data

(60) Provisional application No. 60/990,971, filed on Nov. 29, 2007.

(51) Int. Cl.
*A61K 6/083* (2006.01)
*A61C 5/10* (2006.01)
*B05D 3/00* (2006.01)
*B05C 11/00* (2006.01)
*B05C 11/02* (2006.01)
*B05C 13/00* (2006.01)
*B05C 13/02* (2006.01)
*B05C 21/00* (2006.01)
*B21F 43/00* (2006.01)
*B23P 13/00* (2006.01)
*G06F 19/00* (2011.01)
*B23K 26/00* (2006.01)

(52) U.S. Cl.
USPC .............. 427/2.26; 118/56; 118/63; 118/500; 219/121.6; 29/896.1; 700/98; 700/119

(58) Field of Classification Search ................. 427/2.26; 118/56, 63, 500; 219/121.6; 29/896.1; 700/96, 700/119
See application file for complete search history.

(56) References Cited

U.S. PATENT DOCUMENTS

| | | | |
|---|---|---|---|
| 5,208,431 A | 5/1993 | Uchiyama et al. | |
| 6,144,008 A | 11/2000 | Rabinovich | |
| 2002/0041818 A1 * | 4/2002 | Abe et al. ........................... | 419/7 |
| 2005/0208168 A1 | 9/2005 | Hickerson et al. | |
| 2009/0025638 A1 * | 1/2009 | Inoue ............................. | 118/712 |

FOREIGN PATENT DOCUMENTS

| | | |
|---|---|---|
| EP | 0 967 067 A1 | 12/1999 |
| EP | 1 911 568 A1 | 4/2008 |
| JP | 2004-344623 * | 12/2004 |
| WO | WO 2007/013240 A1 | 2/2007 |

OTHER PUBLICATIONS

"Computer-assisted milling of dental restorations using a new CAD/CAM data acquisition system," Jurgen Willer et al. The Journal of Prosthetic Dentistry, vol. 80, No. 3 (Sep. 1998), pp. 346-353.*

* cited by examiner

*Primary Examiner* — Patricia L Hailey

(57) ABSTRACT

Systems and methods disclosed herein employ various modes of material deposition and material removal to build a complex, three-dimensional structure upon a rotating base. The systems and methods may be usefully employed to fabricate geometrically and aesthetically accurate dental articles from digital models.

20 Claims, 6 Drawing Sheets

THREE-DIMENSIONAL FABRICATION

CROSS REFERENCE TO RELATED APPLICATIONS

This application is a national stage filing under 35 U.S.C. 371 of PCT/US2008/084792, filed Nov. 26, 2008, which claims priority to U.S. Application No. 60/990,971, filed Nov. 29, 2007, the disclosure of which is incorporated by reference in its/their entirety herein.

BACKGROUND

This invention relates to rapid manufacturing, and more particularly to rapid manufacturing items such as dental prosthetics.

Dental restorations may have multiple, complex structures including layers of various materials with different mechanical and aesthetic properties. This poses significant challenges for conventional rapid prototyping systems. Many fabrication technologies employ a single material, which limits output to monolithic structures. Some layer-additive techniques are capable of producing multi-material structures, such as the system described in U.S. Pat. No. 5,208,431 to Uchiyama et al. However, these technologies also impose limitations. For example, layer-additive technologies based on planar deposition of multiple materials have significant issues related to oxidation, thermal stress, and the like. Planar layer additive technologies can also exhibit poor surface qualities due to z-axis stair stepping or x-y plane terracing. Planar strata are also prone to poor layer adhesion which can compromise structural integrity. On the other hand, rotational deposition systems have been devised for fabrication of optical fiber preforms using various mixes of materials; however, these vapor deposition systems focus on uniform circular geometries and are entirely unsuitable for fabrication of custom, three-dimensional shapes.

There remains a need for a system capable of fabricating complex, multi-material items for use in dentistry or the like.

SUMMARY

Systems and methods disclosed herein employ various modes of material deposition and material removal to build a complex, three-dimensional structure upon a rotating base. The systems and methods may be usefully employed to fabricate geometrically and aesthetically accurate dental articles from digital models.

In one aspect, a method disclosed herein includes positioning a stem in a base; rotating the base; and depositing a material on the stem under computer control to create a workpiece, the workpiece having a shape including an interior surface determined by the stem and an exterior surface determined by computer-controlled deposition of the material.

The method may include milling the exterior surface of the workpiece to refine the shape. Milling the exterior surface of the workpiece may include moving a cutting tool through an arc to shape a computer-controlled location on the workpiece. Milling the exterior surface of the workpiece may include moving a cutting tool through a translation in position to shape a computer-controlled location on the workpiece. The method may include sintering the material on the stem. The method may include curing the material on the stem by photopolymerization. The method may include controlling a temperature of a region of the workpiece with a laser. The method may include selectively directing two or more lasers at the workpiece. The method may include controlling a temperature of the workpiece with a directed energy process selected from the group comprising radiant heat and microwaves.

Depositing the material may include spraying the material in a powder form and heating the exterior surface of the workpiece with a laser where the material is to be applied to the workpiece. The method may include measuring a position of the exterior surface of the workpiece. The method may include comparing the position to a digital model and shaping material to conform the workpiece to the digital model. The digital model may include a model of a dental restoration. The method may include shaping an exterior surface of the stem to correspond to an interior surface of the digital model. The method may include affixing a coping to the stem before depositing material. The method may include shaping the surface of the stem to correspond to a surface of a coping. The method may include removing the workpiece from the stem and inserting the coping into the workpiece. Depositing the material may include depositing the material in a continuous spiral deposition pattern. Depositing the material may include controlling a rotation of the base to selectively present surfaces of the workpiece to a deposition head. The method may include bidirectionally rotating the base while depositing the material. Depositing material may include spraying material through a deposition head. The method may include moving the deposition head through an arc to deposit material at a computer-controlled location on the workpiece. The method may include translating the deposition head in position to deposit material at a computer-controlled location on the workpiece. The method may include translating a position of the base relative to at least one of a deposition head and a cutting tool. Depositing the material may include depositing material at a varying rate. Depositing the material may include depositing two or more materials. The method may include mixing the material with a pigment to control coloration of the material before depositing the material. Depositing the material may include selectively spraying one or more materials through two or more deposition heads.

In another aspect, a system disclosed herein includes: a rotating base supporting a stem; a spray deposition head operable to deposit a material on the stem, thereby building up a workpiece, and further operable to deposit the material onto the workpiece in an additive fabrication process; a laser operable to control a surface temperature of the workpiece by application of light from the laser; a cutting device operable to selectively to remove portions of the material from the workpiece; and a controller to control operation of the rotating base, the spray deposition head, the laser, and the cutting device to fabricate a three-dimensional structure from the material according to a digital model.

The system may include a plurality of spray deposition heads, each operable to deposit a material on the stem or the workpiece. The spray deposition head may selectively apply one or more of a plurality of materials under control of the controller. The spray deposition head may selectively mix one or more additives into the material. The one or more additives may include at least one pigment. The material may include a material selected from the group comprising a glass, a porcelain, and a ceramic. The material may include a polymer. The system may include a working volume surrounding the stem and the spray deposition head, the working volume isolated from a surrounding environment. The working volume may be filled with an inert gas. The working volume may be evacuated to provide a vacuum environment. A temperature of the inert gas may be controlled to modify a temperature of the workpiece. The digital model may include a dental restoration. The digital model may include a crown. The digital model may include a multi-material dental restoration.

BRIEF DESCRIPTION OF THE DRAWINGS

The invention and the following detailed description of certain embodiments thereof may be understood by reference to the following figures.

DETAILED DESCRIPTION

Figure 1:
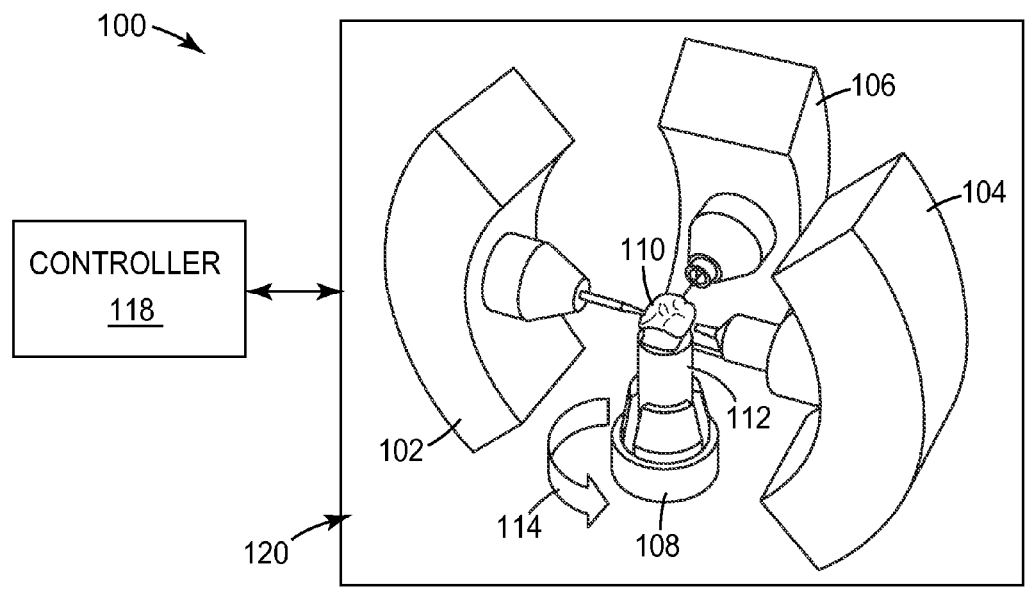
FIG. 1 shows a system for deposition and removal of material using a rotating base.

The term "dental object", as used herein, is intended to refer broadly to dental subject matter. This may include intraoral structures such as dentition, (typically although not exclusively human dentition) including individual teeth, quadrants, full arches, pairs of arches (which may be separate or positioned in various occlusal relationships), soft tissue, and the like, as well as bones and any other supporting or surrounding structures. As used herein, the term "intraoral structures" refers to both natural structures within a mouth as described above and artificial structures such as any of the dental objects described below that might be present in the mouth. As used herein, the term dental article is intended to refer to a man-made dental object. Dental articles may include "restorations", which may be generally understood to include components that restore the structure or function of existing dentition, such as crowns, bridges, veneers, inlays, on-lays, amalgams, composites, and various substructures such as copings and the like, as well as temporary restorations for use while a permanent restoration is being fabricated. Dental articles may also include a "prosthesis" that replaces dentition with removable or permanent structures, such as dentures, partial dentures, implants, retained dentures, and the like. Dental articles may also include "appliances" used to correct, align, or otherwise temporarily or permanently adjust dentition, such as removable orthodontic appliances, surgical stents, bruxism appliances, snore guards, indirect bracket placement appliances, and the like. Dental articles may also include "hardware" affixed to dentition for an extended period, such as implant fixtures, implant abutments, orthodontic brackets, and other orthodontic components. Dental articles may also include "interim components" of dental manufacture such as dental models (full or partial), wax-ups, investment molds, and the like, as well as trays, bases, dies, and other components employed in the fabrication of restorations, prostheses, and the like. Dental objects may also be categorized as natural dental objects such as the teeth, bone, and other intraoral structures described above or as artificial dental objects (i.e., dental articles) such as the restorations, prostheses, appliances, hardware, and interim components of dental manufacture as described above. A dental article may be fabricated intraorally, extraorally, or some combination of these.

The three-dimensional fabrication systems described herein may also or instead be employed to fabricate structured billets for milling or pressing. A billet may include any unfinished material that is being formed into finished product. In dental applications, the structured billet may include a block of material containing a specific gradient of material properties such as hardness, color, translucence, and the like. Although the following description focuses on dental applications, the techniques described herein may also suitably be adapted to other rapid prototyping and fabrication systems, and all such variations that would be apparent to one of ordinary skill in the art are intended to fall within the scope of this disclosure.

While the following description emphasizes deposition of ceramics on a rotating workpieces, it will be understood that similar techniques may be employed with a wide range of materials to construct geometrically accurate three-dimensional articles in an additive manner. Many such alternative materials are noted below, all by way of example and not of limitation.

FIG. 1 shows a system for deposition and removal of material using a rotating base. The system 100 may include a cutting device 102, a spray deposition head 104, a laser 106, and a base 108 supporting a workpiece 110 on a stem 112 within an operative distance of the cutting device 102, the deposition head 104, and the laser 106. The system 100 may be controlled by one or more controllers 118, and the system 100 or various components thereof may be enclosed in a working volume 120 isolated or otherwise separated from the surrounding atmosphere. The isolation may, for example include vacuum isolation, or any other separation useful for maintaining an environment that is particle-free, temperature controlled, moisture-free, or otherwise free from unwanted substances. Similarly, the working volume may be employed to provide an inert gas environment or otherwise preserve a working environment separated from ambient conditions and suitable to a desired fabrication process.

The cutting device 102 may be a high-temperature diamond ceramic cutter suitable for milling or otherwise cutting high hardness substances. More generally, the type of cutting tool employed by the cutting device 102 may vary according to the type of material forming the workpiece 110. Similarly, the type of cutting tool may vary according to the characteristics, such as temperature, of the workpiece being operated upon. The workpiece may comprise substances including metals, porcelain, ceramics, thermoplastics, thermosets, photopolymers, and so forth. In embodiments, the cutting device 102 may have multiple cutting heads for different types of materials. The cutting device 102 may have a controllable rotational orientation, as generally indicated by the arced shape thereof to permit the cutting device 102 to engage the workpiece 110 at different angles. Thus, the cutting device 102 may move in an arc or the like to shape various surfaces of the workpiece 110. The cutting device 102 may also provide translational movement including movement toward or away from the axis of the base 108, and along various axes useful for positioning the cutting device 102 to remove material from the workpiece 110. Many computer-controlled milling devices are known and may be suitably adapted for use as the cutting device 102 described herein.

The spray deposition head 104 may provide numerous degrees of translational and rotational freedom as generally described above for the cutting device 102. The spray deposition head 104 may be any device suitable for depositing controlled quantities of material onto the stem 112 and/or workpiece 110, and may vary according to the type or types of materials to be deposited. A variety of suitable spray heads are known for ceramic or glass deposition and the like, such as chemical vapor deposition spray heads. In addition, a variety of three-dimensional and inkjet printing techniques are known in the art for use in depositing controlled amounts of a material at a controlled location, any of which may be adapted to use as a spray deposition head 104 as that term is used herein, according to the various materials that might be deposited using the systems and methods described herein.

In one embodiment, heated argon may carry micro-ceramic particulates into the path of a laser where particles are melted and deposited in thin film on the workpiece 110. Any particles outside the laser beam may remain unsintered and be collected and reused by the deposition head 104. The laser beam may be defocused and focused to vary the deposition rate or deposition accuracy as needed by the deposition process. The spray deposition head 104 may permit selection among different materials. This may include multiple jets or nozzles for various materials, as well as multiple containers with different materials (e.g., having different colors or other properties) that can be mixed by a single nozzle. For example, in order to deposit complex, aesthetic layers for fabrication of a dental article, various pigments may be introduced to control optical characteristics of deposited glass within a defined dental color space. Similarly, a number of different sources of colored substances may be mixed under computer control to obtain a desired shade, opacity, or the like. The combination of multiple colored substances may achieve a multi-chromatic article more closely resembling natural dentition. It may be advantageous to orient the spray deposition head 104 above a deposition layer to utilize gravitation to form a consistent, continuous, spatially-controlled powder beam. Thus in one embodiment, the base 108 may support a workpiece 110 on a substantially horizontal axis, with the deposition head 104 and an accompanying laser directly above a deposition surface of the workpiece 110. In such embodiments, the base 108 may rotate the workpiece 110 about the horizontal axis, and other components such as the laser 106 and cutting device 102 may be positioned below or along side the workpiece 110. In another embodiment, a center axis of the base 108 may be rotated so that a top of the stem 112 initially presents a horizontal surface, and when a workpiece 110 has been created, the workpiece 110 may be rotated so that any surface thereof may be presented in a horizontal orientation for improved deposition.

The laser 106 may be, for example, a focused $CO_2$ laser that operates to control temperature of the workpiece 110 during deposition. In particular, the laser 106 may sustain a desired temperature for any deposited layers to enable densification and flow of the deposited material. It will be understood that, while a focused $CO_2$ laser can provide heating suitable for the types of ceramics generally contemplated for use as an exterior layer of dental articles, other lasers may be similarly employed according to the type of material deposited and the temperatures required for curing, sintering, flowing, bonding or otherwise controlling and/or processing deposited material. By way of example an ultra violet laser may be employed to initiate photopolymerization of a deposited photopolymer composite. Temperature control may also be important for maintaining a molten or fluid state, or otherwise improving adhesion and or initiating welding and fusing among successive layers of deposited material. While the system 100 may provide a laser 106 with rotational and translational control as described above, a suitable laser may also be fixed, or provide targeting across a useful x-y plane with two rotational degrees of freedom. In embodiments where polymers are employed, the laser 106 may be replaced with a catalyst source or other curing agent to selectively cure the deposited polymer. For certain applications, other energy sources such as radiant heat or microwaves may be utilized. An apparatus may be employed allowing selection of one or more of a laser, radiant heat, or a microwave source.

In one embodiment, shaping by the cutting device 102 may be performed prior to curing, sintering, or other hardening. This may advantageously speed cutting time and/or extend the useful life of a cutting tool on the cutting device 102.

The base 108, may support a workpiece, and may rotate in order to present various surfaces of the workpiece 110 to the deposition head 104, laser 106, and cutting device 102 during processing. In one aspect, deposition may be performed in a continuous, spiral action with a constantly rotating base. In other embodiments, the base 108 may rotate bi-directionally. The base 108 may also provide translational movement in order to control the distance of the workpiece 110 from the cutting device 102, deposition head 104, and/or laser 106. Rotation of the base 108 about a center axis is generally depicted by an arrow 114; however, it will be understood that the center axis may also be rotated such as to horizontally orient various surfaces of the workpiece 110 as noted above.

The workpiece 110 may be any article three-dimensionally created using a build-up of material from the deposition head 104. In addition, the workpiece 110 may be subtractively shaped using the cutting device 102, such as to remove overspray or to add features difficult to obtain using deposition alone, such as thin layers of fine detail. The cutting device 102 may also enable the generation of layers thinner than the viscosity and surface tension of the spray deposited material allow. In one aspect, the workpiece 110 may be a ceramic crown or other dental article.

The stem 112 may be a plaster or graphite billet that will not securely adhere to the deposition material. In the case of photopolymer composites, a hard wax stem may be used. A water-soluble polymer stem may also or instead be employed. In one aspect discussed in greater detail below, the stem 112 may be milled by the cutting device 102 into the form of a prepared tooth surface (e.g., a site in a dental patient's dentition where a restoration will be placed), or into the form of a coping to which the workpiece 110 is to be attached. The stem 112 may be shaped to match the interior shape of such a coping so that the coping can be subsequently pressed into the crown or otherwise attached thereto. Clearance compensations may be incorporated into a surface of the stem 112. Three-dimensional data for such surfaces of a crown, coping, and/or prepared tooth surface may be obtained using any suitable three-dimensional data acquisition technology.

A controller 118 may be provided to control operation of the cutting device 102, the spray deposition head 104, the laser 106, and the base 108, as well as any other components associated with the system 100. For example, the controller 118 may control a position, orientation, and rotational speed of the cutting device 102, as well as activation of the cutting device 102 and selection of a cutting tool therefore. The controller 118 may control operation of the spray deposition head 104 by controlling a position and orientation of the tool, as well as the flow rate of material delivered therefrom. The controller 118 may further control additives or material mixtures for the spray deposition head. The controller 118 may control activation of the laser and may direct the laser toward a desired point or region of the workpiece 110, such as to prepare a surface of the workpiece 110 for deposition, to flow material deposited on the workpiece, or more generally to control a temperature, cure a material, or otherwise assist in processing as described herein. The controller 118 may control operation of the base 108, such as by controlling a rotational speed and/or direction of the base 108 in a deposition process, or by controlling the axial position and orientation of the base 108 in order to move the workpiece 110 into a desired location relative to the various tools of the system 100. Still more generally, the controller 118 may control any components of the system in order to process the workpiece 110 as described herein. In general, the controller 118 controls operation of the system components to fabricate an object according to a digital model, such as a model of a dental restoration. The digital model may include a spatial description of an object such as a volumetric or surface representation of the object, along with other spatial information such as hardness, color, opacity, and the like at various locations of the object.

It will be appreciated that the controller 118 may include, and the processes described below may be embodied in, any hardware, software, or combination of these suitable for use with the rapid fabrication systems and methods described herein. The hardware may include a general purpose computer and/or dedicated computing device. The processes described below, which may in whole or in part be executed by the controller 118, may be realized in one or more microprocessors, microcontrollers, embedded microcontrollers, programmable digital signal processors or other programmable device, along with internal and/or external memory. The processes may also, or instead, be embodied in an application specific integrated circuit, a programmable gate array, programmable array logic, or any other device that may be configured to process electronic signals. It will further be appreciated that the process may be realized as computer executable code embodied on a computer readable medium that, when executing on one or more computing devices, performs the recited steps. The computer executable code may, for example, be created using a structured programming language such as C, an object oriented programming language such as C++, or any other high-level or low-level programming language (including assembly languages, hardware description languages, and database programming languages and technologies) that may be stored, compiled or interpreted to run on one or more of the above devices, as well as heterogeneous combinations of processors, processor architectures, or combinations of different hardware and software. At the same time, processing may be distributed across a number of different computing devices in a number of ways, or all of the functionality may be integrated into a dedicated, standalone device or other hardware. All such permutations and combinations are intended to fall within the scope of the present disclosure.

Other devices may also be included in the system 100. For example, any number of additional lasers or other heating and temperature measurement devices might be usefully employed to manage a thermal state of the stem 112 and/or workpiece 110. In an embodiment, one laser may be directed ahead of the melt front for a deposition path to pre-heat the previous layer to a state where it initiates welding with a subsequent layer. In this case, welding refers to a strong structural adherence or joint between layers and/or materials, as distinguished for a loose intermingling or mix which might result in poor adhesion or aesthetics at layer boundaries. A second laser may, for example, be directed behind the melt front to enable flow and densification. Other devices may include air handlers, vacuum handlers, utilities (gas, electricity, cutting tool lubricants, deposition material supplies, etc.), active cooling systems, heating elements, radiant heat sources, microwave sources (e.g., for heating) and so forth, any of which may be usefully employed in fabrication processes as described herein. In addition, a variety of sensors may be employed. For example, spatial measurement systems may be employed to ensure that a combination of deposition and material removal are deployed to create a desired shape of the workpiece 110. Temperature measurement systems may be employed to monitor a temperature at a location on the workpiece 110, or to monitor ambient temperature, and so forth. All such tools and sensors and variations of any of the foregoing are intended to fall within the scope of this disclosure. In one aspect, a combination of sensors and tools provides a feedback system to control deposition and/or material removal to achieve a desired final shape of the workpiece 110.

The entire system 100 may be enclosed in a working volume 120 which may be isolated from the surrounding, ambient atmosphere. Within the working volume 120, the working environment may be controlled to achieve a desired temperature, pressure (or vacuum), humidity, and the like, as well as to control the introduction or purging of gasses such as inert gasses that might be used to improve deposition or other material handling operations. In addition, any combination of the foregoing may be employed within the working volume 120 to control a fabrication process as described herein. For example, an inert gas may be heated or cooled and directed at the workpiece 110 to control a temperature thereof during deposition, or the working volume 120 may be evacuated to provide a vacuum environment for some or all of a deposition process. All such variations that would be apparent to one of ordinary skill in the art are intended to fall within the scope of this disclosure.

Figure 2:
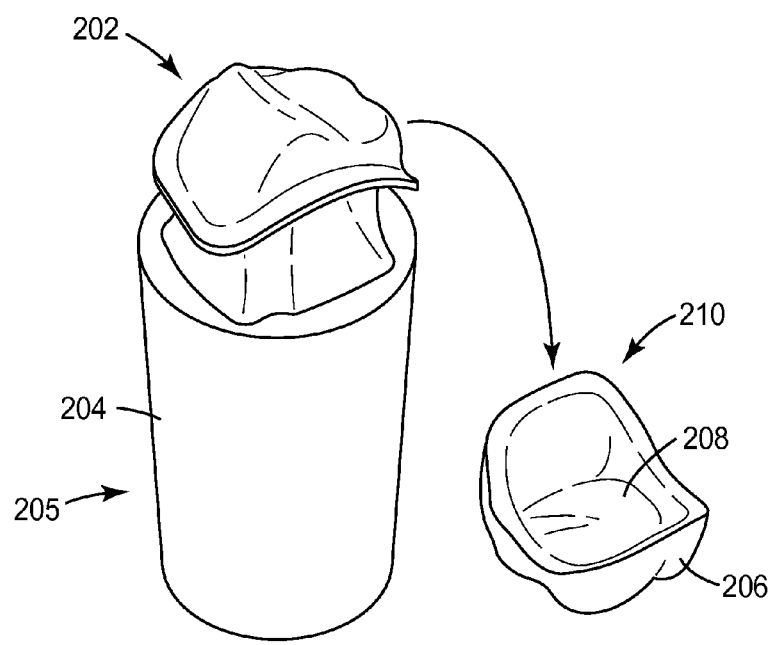
FIG. 2 shows a crown fabricated using the device of FIG. 1.

FIG. 2 shows a crown fabricated using the system of FIG. 1. As can be seen in FIG. 2, a stem 204 provides a starting point for construction of a workpiece, and includes a first portion 205 for insertion into a base (not shown) and a top surface 202 that provides a physical starting point for additive creation of a crown 206 or other workpiece. The stem 204 may be comprised of a billet. The top surface 202 may be formed into the shape of a prepared tooth surface, which shape may be achieved by cutting the stem using, e.g., the cutting device described above. By way of example, the crown 206 may be fabricated as a ceramic crown using deposition and/or cutting directly on the top surface 202 of the stem 204. The crown 206 may be removed after fabrication is complete. An interior surface 208 of the crown 206 may be defined by the top surface 202 on the stem 204. An exterior surface 210 of the crown 206 may be determined by a digital model or the like and created during an additive deposition process as generally described herein.

In one aspect, the top surface 202 may be shaped to match a surface of a coping or the like, and the coping may be affixed to the interior surface 208 of the crown 206 after the crown 206 is removed from the stem 204. In embodiments, the stem 204 may be formed of a material that can be readily separated from the deposited material, as generally described above. In embodiments, a film or the like may be applied to the top surface 202 of the stem 204 to facilitate temporary bonding and later removal of the deposited material.

It will be understood that, while a crown is depicted in FIG. 2, the methods and systems described herein may be used to fabricate a wide array of dental objects such as bridges, onlays, inlays, dentures, and any other dental objects noted above, as well as other dental objects and more generally, any object having a size, shape, and material properties amenable to fabrication using the techniques described herein.

Figure 3:
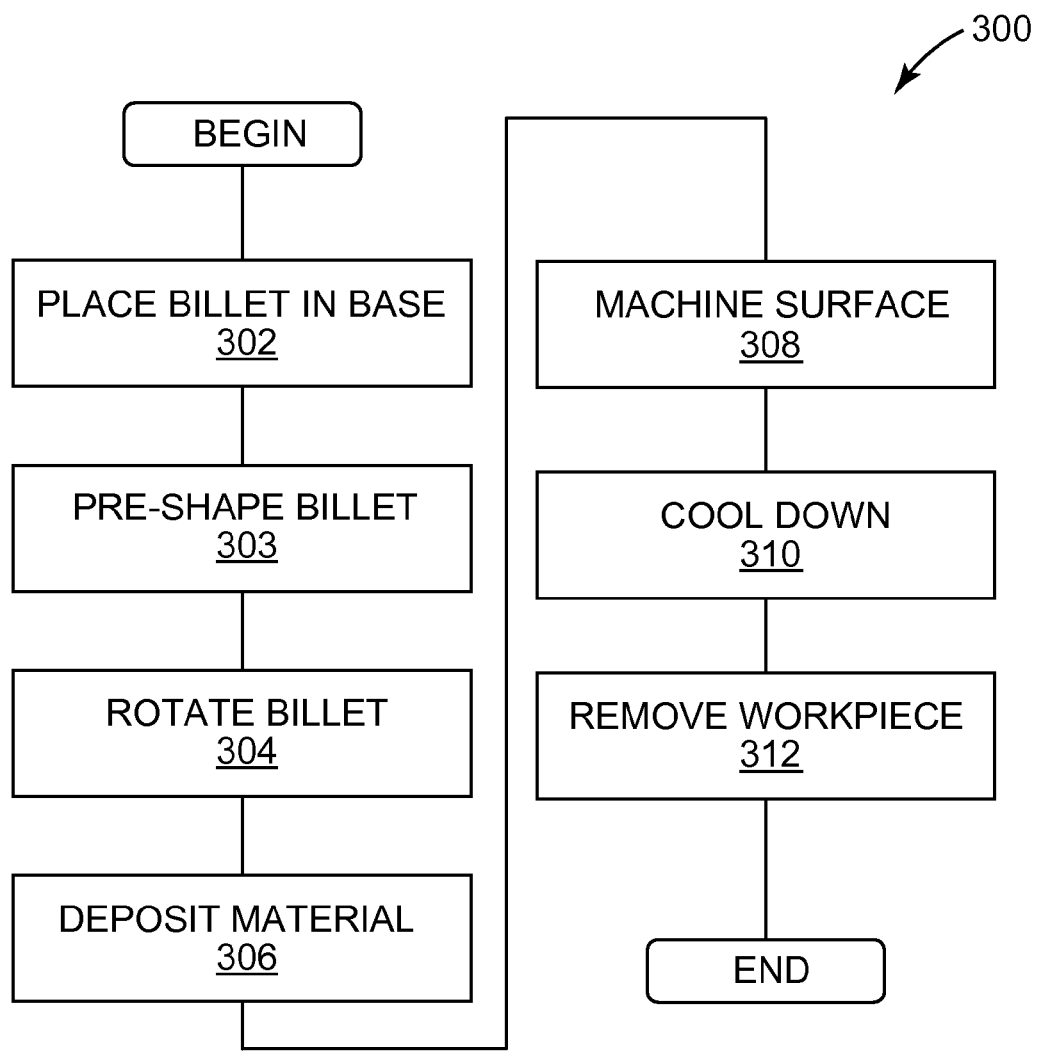
FIG. 3 shows a process for fabricating a dental article.

FIG. 3 shows a process for fabricating a dental article using the systems described above.

As shown in step 302, the process 300 may begin by placing a billet into the base of a fabrication system, which may be the system 100 described above. For ceramic deposition, a plaster or graphite billet may be usefully employed; however, it will be understood that the material used for the billet may vary according to the particular deposition process. For example, a wax billet may be used to receive deposition of a photopolymer composite. A build chamber encompassing the working volume described above may be filled with argon or some other inert gas suitable to the materials being processed, and heated as appropriate for a particular fabrication process. Depending upon the material being deposited, the chamber temperature may be 500° C. or greater. In other embodiments, such as a process employing a photopolymer composite, the chamber may be significantly cooler.

As shown in step 303, the billet may be pre-shaped, e.g., using the cutting device of the system, to correspond to a target shape for a surface of the workpiece. Thus one surface of the workpiece (where the workpiece abuts the billet) is shaped by physically conforming to the billet surface. It will be understood that, while the billet may usefully be shaped using the cutting device of the system, other techniques may usefully be employed to shape the surface of the workpiece where it abuts the billet. This includes, for example, pre-shaping the billet before it is placed into the base, which requires some form of alignment before deposition begins (e.g., by fabricating the billet so that it mechanically registers to a spatially unique location in the base, or by using measurement tools of the system to determine a position and orientation of the pre-shaped surface before starting deposition). This may also include milling or otherwise shaping the surface after removing the workpiece from the billet.

Where the dental article (or other item) includes a prefabricated sub-structure such as coping fabricated from zirconium, alumina, cast metal alloy, or other materials, the sub-structure may be separately fabricated and placed onto the billet after shaping. In such arrangements, it will be understood that the billet does not need to be pre-shaped to any specific form. Rather, any shape that can retain the substructure (such as by using a curable billet or any suitable adhesive) may be employed, provided the substructure can be readily removed from the billet after completion of the process 300.

As shown in step 304, the base may be rotated so that surface regions of the billet are progressively presented to the system tools. In one aspect, a fixed speed of rotation is employed for continuous, spiral deposition of a workpiece onto the billet. In another aspect, the speed may be variable and/or bi-directional so that various surfaces of the workpiece can be selectively presented to the spray deposition head, laser, cutting device, etc. The base may also be moved transversely in x, y, and/or z dimensions so that a desired portion of the billet (or a workpiece constructed on the billet) may be shaped. Similarly the base may be moved radially through an angle to orient a working surface of the workpiece relative to the cutting device, laser, deposition spray head, and/or other system tools.

As shown in step 306, material may be deposited—initially directly onto the billet, but subsequently onto a workpiece built up on the billet—to achieve a shape desired according to a digital model or the like. Excess material may also be deposited at a location on the workpiece in order to accommodate subsequent removal to a desired dimension, thickness, or the like. As noted above, deposition of various materials may be included in order to build-up a multi-colored or multi-chromatic porcelain or ceramic exterior for a dental article that mimics the color, opacity, and the like of natural dentition. Overspray of excess material may be collected and recycled for subsequent use.

As shown in step 308 the workpiece may be milled to a target shape, thus providing control over shape, thickness, or surface feature definition not otherwise possible with deposition. It will be understood that, while rotating the billet 304, depositing material 306, and machining the surface 308 are depicted as three sequential steps, these steps may be performed numerous times in any desired order, or concurrently, or some combination of these, all without departing from the scope of this disclosure. Thus, a continuous, rotating, deposition and milling process may be employed under computer control to form a workpiece on the billet according to a digital model.

As shown in step 310, the build chamber may be cooled down. Cooling may be accomplished by pumping coolant through the base or other fixture portions. Cooling may also be accomplished by providing an inert gas at a lower temperature into the chamber. The cooling process may be utilized to quench the workpiece in order to aid in fabrication of a chemical or mechanical property for the material comprising the workpiece. The cooling process may also or instead be used to bring the workpiece to a particular temperature, such as a lower temperature for handling.

As shown in step 312, the workpiece may be removed from the billet, and the process 300 may end.

It should be understood that the steps shown in FIG. 3 may be modified, or the order of steps may be changed. Further, individual steps may be omitted, and other steps may be added, all without departing from the scope of this disclosure. The step sequence shown in the flow chart of FIG. 3 is provided for illustrative purposes only, and does not limit the scope of the disclosed process unless explicitly stated to the contrary or otherwise clear from the context. By way of example, in certain embodiments the pre-shaping of the billet may be omitted entirely, or may be performed before placing the billet in the base. As another example, the steps of rotating 304, depositing 306, and machining 308 may be performed continuously, alternately, in a repeating sequence, or in some other pattern, as well as any combination of these. It will further be understood that any of a variety of pre-processing and/or post-processing steps may be performed, such as polishing, baking, curing, sintering, coating, cleaning, and so forth, all without departing from the scope of the invention.

In another aspect, the methods and systems described herein may be usefully employed to create a composite billet or other milling blank that contains a variety of materials with different properties distributed within the billet according to a digital model according to a desired end product. For example, a general interior region may be fabricated to provide low weight, high thermal conductance, high strength, and so forth, while a general exterior region may be fabricated to provide high hardness, polishability, opaqueness (or translucence), color, and so forth. More generally, any combination of materials having any useful combination of properties may be distributed within a billet fabricated using the techniques described herein. A resulting billet may be subsequently machined into a precise exterior shape using milling or the like (such as in a computer-controlled milling machine), resulting in an item having a shape corresponding to a digital model and an interior having various regions with different materials and/or properties.

Figure 4:
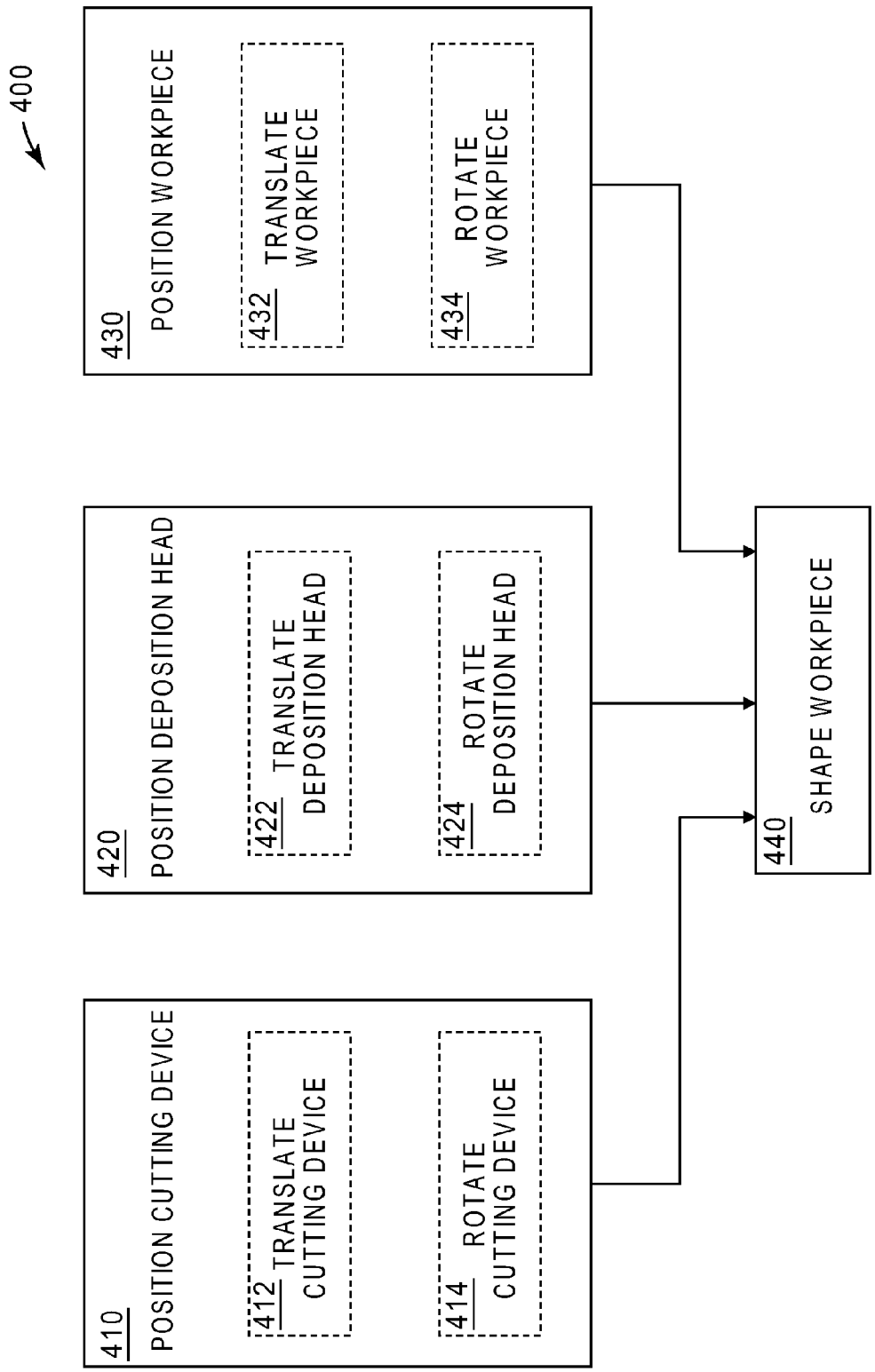
FIG. 4 shows a flow chart for positioning of a workpiece and/or tools.

FIG. 4 shows an exemplary flow chart for positioning of the workpiece and/or the tools to accomplish the desired fabrication. It should be understood that the steps shown in FIG. 4 may be modified in order, or may be performed concurrently. Further, individual steps may be optionally performed or omitted in certain circumstances. The step sequence shown in the flow chart of FIG. 4 is only shown for the purpose of illustrating various processing steps that may contribute to shaping a workpiece as described herein.

In a general fabrication process 400, some combination of positioning a cutting device 410, positioning a spray deposition head 420, and positioning a workpiece 430 may be performed. For certain use cases all of these positioning aspects may be employed in combination, or only one or two of the aspects may be used. These positioning capabilities may be combined and applied to create and shape a workpiece 440 as desired.

A cutting device such as any of the cutting devices described above may be positioned 410. The aspects of positioning of the cutting device may include translating the cutting device 412 and rotating the cutting device 414. Either rotating or translating may take place first. Similarly, only one or none of these positioning capabilities may be utilized in any given fabrication process.

A spray deposition head such as any of the spray deposition heads described above may be positioned 420. The aspects of positioning of the deposition head may include translating the deposition head 422 and rotating the deposition head 424. Either rotating or translating may take place first, and/or both operations may occur simultaneously. Similarly, only one or none of these positioning capabilities may be utilized in any given fabrication process.

A workpiece 110, as previously illustrated, may be positioned 430. The aspects of positioning of the workpiece may include translating the workpiece 432 and rotating the workpiece 434. The translating of the workpiece may be in any of the x, y, and z dimensions or some combination of these. Either rotating or translating may take place first. The workpiece may also be radially moved through an arc to present a surface of the workpiece in various orientations to the various tools. In one aspect, the workpiece may be positioned beneath the spray deposition head so that gravity assists with direction of a sprayed material toward the surface of the workpiece. In one aspect, the workpiece may be rotated continuously in the base in a continuous spiral deposition process.

The steps shown in FIG. 4 may be implemented in a different order than shown or described. Likewise certain steps may be omitted in certain fabrication situations. Additionally some steps may be repeated. For instance, the cutting device may be repeatedly translated or rotated as the workpiece is shaped. The deposition head may be repeatedly translated or rotated. The workpiece may also be repeatedly translated or rotated. Similarly, a combination of cutting device, deposition head, and workpiece positioning may be implemented. Thus the steps of FIG. 4 are only exemplary in nature and are not intended to restrict the scope or spirit of the invention.

Figure 5:
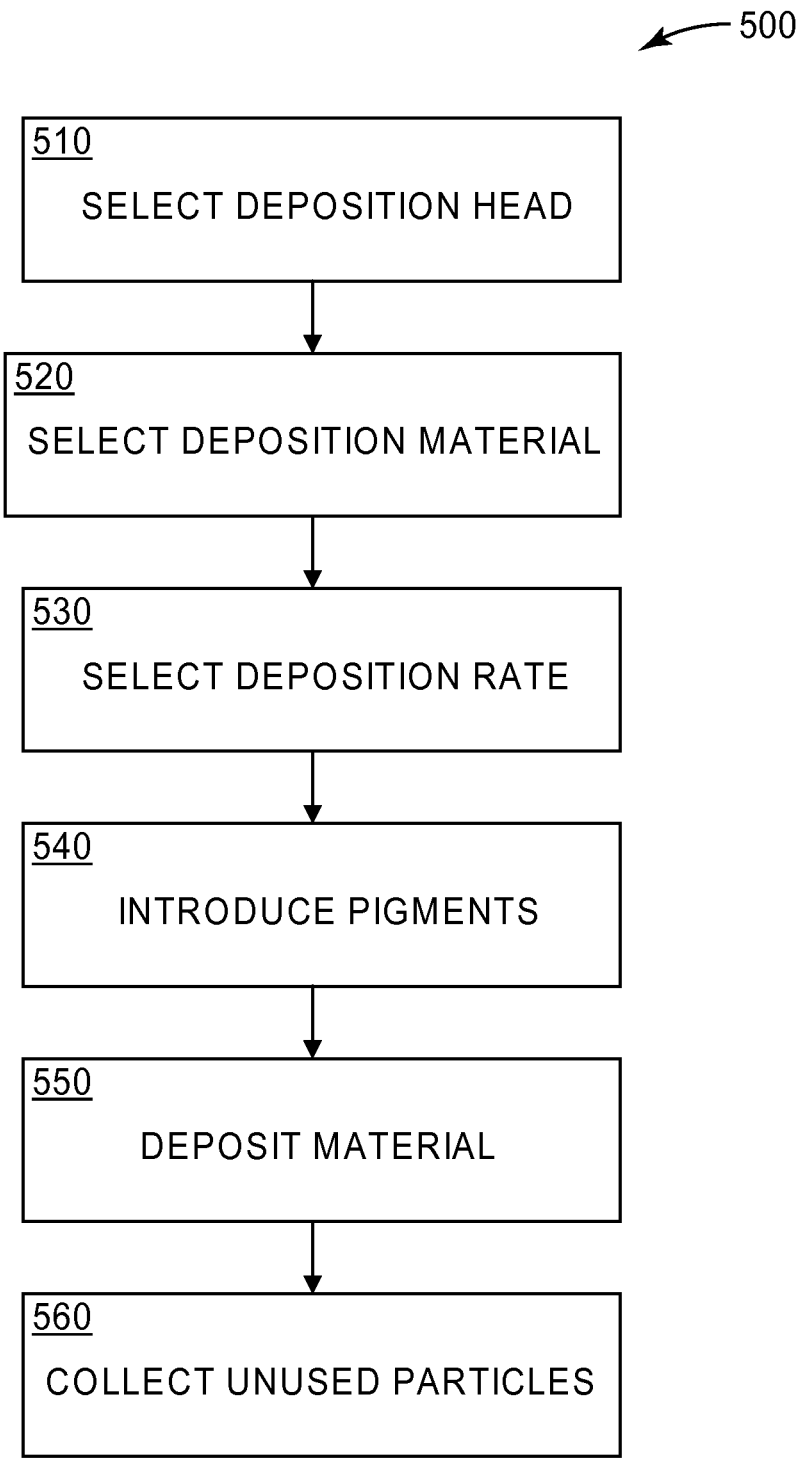
FIG. 5 shows a flow chart for a spray deposition process.

FIG. 5 shows a flow chart for a spray deposition process. It should be understood that the steps shown in FIG. 5 may be modified in order. Further, individual steps may not be performed in certain circumstances. The step sequence shown in the flow chart of FIG. 5 is only shown for illustrative purposes.

The process may begin with a selection of a spray deposition head, as shown in step 510. In embodiments, multiple deposition heads may be available. Different heads might be employed, for example, to accommodate different deposition rates, deposition layer thicknesses, material types, and so forth. Based on the possible materials being deposited or even based on the ultimate desired shape of the workpiece, different deposition heads may be useful. More generally, one of a plurality of deposition spray heads may be selected by the controller according to the digital model of the object being fabricated.

As shown in step 520, a deposition material may be selected. In embodiments, the system may provide various types and consistencies of materials for spray deposition. When multiple deposition materials are utilized one of these deposition materials may be selected at a time. Differing deposition materials may be desired to achieve differing hardness levels, differing thermal coefficients of expansion, differing melting points, or any other chemical, mechanical, and/or aesthetic properties. One of these deposition materials may be selected at a particular point in the fabrication process, such as for a general or specific layer of material in a three-dimensional structure. More generally, the deposition material may be selected by the controller according to the digital model of the object being fabricated.

As shown in step 530, a deposition rate may be selected. Differing deposition rates may be desired based on specific applications. Deposition rates may affect the thickness of a specific layer, the resulting surface roughness, or other chemical, mechanical, or aesthetic properties. The deposition rate may be selected by the controller according to the digital model for the object being fabricated.

As shown in step 540, pigments or other additives may be introduced into the material being deposited. Pigments or additives may be mixed with the deposition material in order to control color, opacity, shade, translucence and the like. Additives may also be provided to enhance or modify strength, hardness, adhesion, melting point, and other properties of the deposition material, and any additives known to one of ordinary skill in the art for such purposes are intended to fall within the scope of this disclosure. The additives may be selected by the controller according to the digital model for the object being fabricated.

As shown in step 550, material may be deposited on the workpiece from the spray deposition head. Once the various parameters for deposition have been determined (spray head, position, rate, etc.), the spray deposition head may be controlled by the controller to deliver material to the workpieces.

Unused particles from the deposition may be collected for later use as shown in step 560. Some portion of the material being ejected from the deposition head may not land on the workpiece, or may remain unsintered, or may otherwise exit from the spray head without being incorporated into the workpiece. This unused material may be collected for later re-use where possible, or simply disposed of.

The steps described in FIG. 5 are only illustrative and may be modified in order. Certain steps may be excluded in specific fabrication cases. Further, additional steps may be included by those of skill in the art. Additionally some steps may be repeated. For instance, different deposition heads, deposition materials, and deposition rates may be repeatedly selected as the workpiece is successively built up. Thus the steps of FIG. 5 are only exemplary in nature and are not intended to restrict the scope or spirit of the invention.

Figure 6:
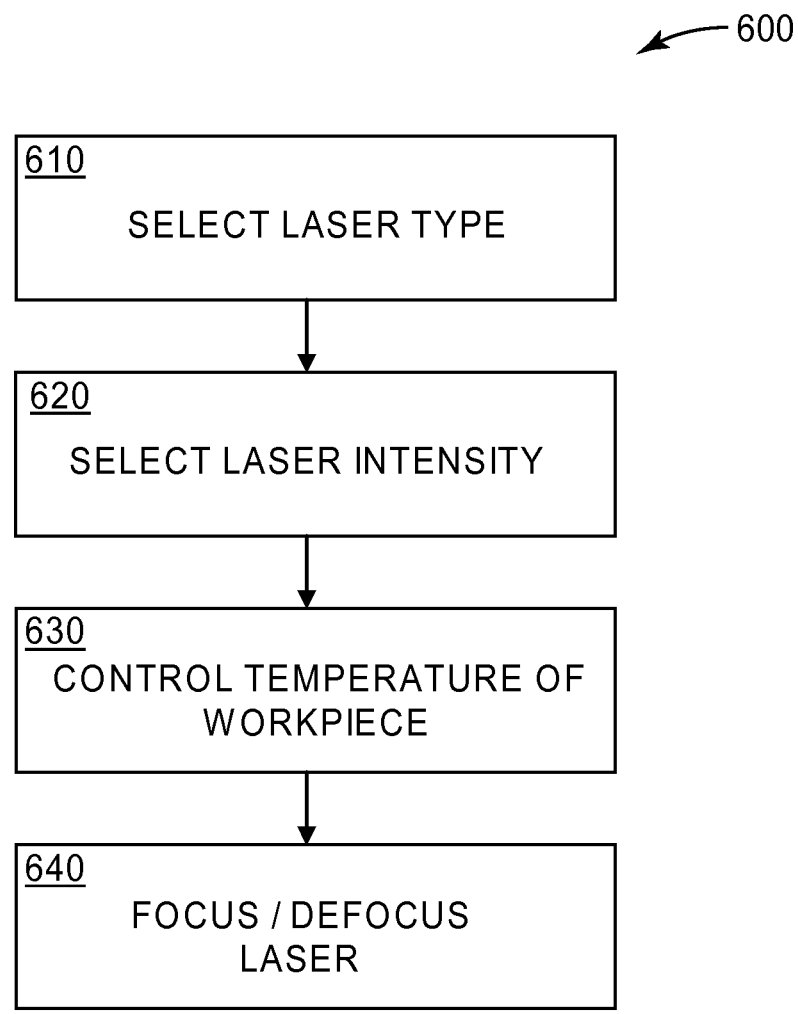
FIG. 6 shows a flow chart for a laser operation process.

FIG. 6 is a flow chart for a laser operation process. It should be understood that the order of steps may be varied, or that individual steps may be modified. In addition, steps may be added to or omitted from the process 600 without departing from the scope of this description. The step sequence shown in the process 600 of FIG. 6 is provided for illustrative purposes only, and not by way of limitation.

As shown in step 610, a laser type may be selected. Certain lasers are useful for manipulating specific materials in the fabrication process based upon, e.g., beam strength, temperature, wavelength, and so forth. In the case where multiple lasers are available in the fabrication process, a particular one of those may be selected for use by the controller according to the digital model and any available sensor data or other information about the workpiece, the deposition process, and/or the ambient conditions.

As shown in step 620, the laser intensity may be selected. This selection may depend, for example, upon the material being deposited or the state of a workpiece (e.g., the temperature, the distance from a spray deposition head, etc.). The controller may select an intensity setting for the laser based upon the digital model and any available sensor data or other information about the workpiece, the deposition process, and/or the ambient conditions.

As shown in step 630, a temperature of the workpiece may be monitored and controlled during the fabrication process. The controller may determine a specific temperature (or temperature range) for the workpiece based upon any appropriate data, and may gather temperature measurements from the fabrication system using any suitable techniques. The laser may then be applied to adjust the temperature of the workpiece or a surface or region of the workpiece (or deposition material before it lands on the workpiece). In general, it will be understood that temperature may be usefully controlled in a fabrication process for any of a variety of reasons including control of the deposition material, layer-to-layer adhesion, malleability (for cutting), curing, flow of deposited material, sintering, and so forth. The controller may determine a constant or varying target temperature and may control operation of the laser to achieve the target temperature at the desired location(s).

As shown in step 640, the laser may be focused or defocused, with a specific focus selected by the controller according to, e.g., the type of material being deposited, the desired rate of deposition, and any other factor(s) that might usefully be applied to determine a suitable laser focus.

The steps shown in FIG. 6 may be implemented in a different order than shown or described. Likewise certain steps may be omitted in certain fabrication situations. Additionally some steps may be repeated. For instance, the laser type and laser intensity may be repeatedly selected as different materials are deposited or different shapes are built up on the workpiece. Thus the steps of FIG. 6 are only exemplary in nature and are not intended to restrict the scope or spirit of the invention.

Figure 7:
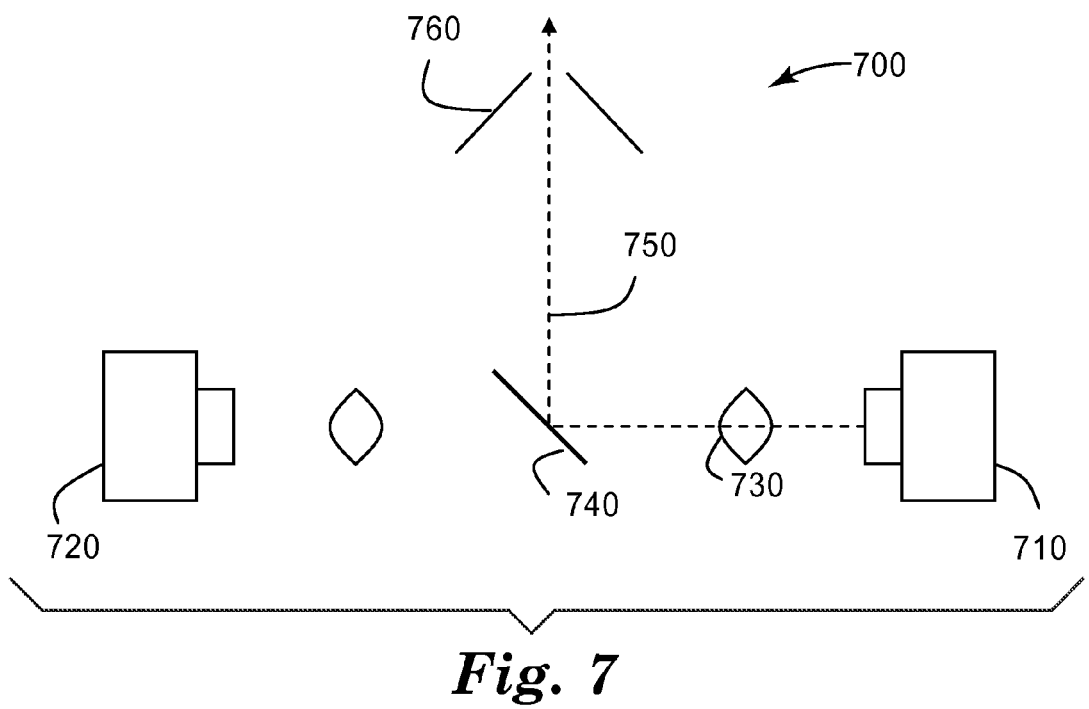
FIG. 7 shows a laser selection tool.

FIG. 7 shows an apparatus 700 for selecting between two lasers. A first laser 710 and a second laser 720 may be provided, such as lasers of different types or lasers having different power ranges. One or both of the lasers may include a focusing lens 730 that focuses and directs light emitted from the laser. A controllable mirror 740 may be selectively rotated to reflect light from one of the lasers 710, 720 through an opening 760, thus directing a laser beam 750 toward the workpiece, such as for any of the purposes described above. The apparatus 700 may select among the lasers 710, 720 by rotating the mirror 740 to reflect a corresponding laser beam 750 through the opening. It will be understood that while two lasers 710, 720 are illustrated, any number of lasers may be usefully incorporated into a multi-laser system that uses a rotating mirror or other beam selection apparatus to select among various laser beams.

It will be appreciated that numerous variations to the above methods and systems are possible, and are contemplated by the current disclosure. For example, while conventional cutting/milling techniques may be usefully employed to shape the workpiece under certain processing conditions, the material within the workpiece might be maintained in a molten, near-molten, or other relatively soft state throughout the deposition process, in which case soft-cutting techniques might alternatively be employed. The temperature and other aspects of the processing environment might also depend upon the type of material being deposited. For glass deposition, an inert gas such as nitrogen or argon might be advantageously used within the deposition chamber to avoid oxidation of deposited materials and other undesirable effects. A vacuum is preferred for sintering. On the other hand, where the deposition process deposits a photopolymer or the like, a different environment (e.g., a moisture-free and oxygen-free environment) may be required for polymerization.

While a $CO_2$ laser may be usefully employed for densifying, melting, or sintering ceramic or porcelain depositions, other laser types might be used to cure polymers. In addition, one or more extra lasers may be provided for pre-heating a surface of the workpiece or maintaining a state of deposited material after deposition.

In general, there is disclosed herein a system in which at least one cutting tool, at least one deposition system, and at least one laser cooperate under computer control to fabricate a three-dimensional shape on a stem based upon a digital model. In one aspect, a three-dimensional article is fabricated using a constant deposition of ceramic onto a rotating stem. The deposition material may be dynamically changed during the build-up to achieve a multi-chromatic article or otherwise control characteristics of the fabricated object. By maintaining the deposition material in a molten or semi-molten state, the system may advantageously improve layer adhesion among deposited layers, reduce porosity, modify optical transmission of restoration, or generate a glazed surface finish, or otherwise improve the fabrication process and/or the fabricated item.

While the invention has been disclosed with preferred embodiments shown and described, various modifications and possible improvements will be readily apparent to those skilled in the art. Thus the spirit of the inventions is not to be limited by the previous exemplary illustrations, and the invention should be interpreted in the broadest sense allowable by law.

What is claimed is:

1. A method comprising:
    positioning a stem in a base;
    milling the stem into a shape of a prepared tooth surface for a dental restoration;
    rotating the base; and
    depositing a material on the stem under computer control to create a workpiece, the workpiece having a shape including an interior surface determined by the stem and an exterior surface determined by computer-controlled deposition of the material according to an exterior shape for the dental restoration.

2. The method of claim 1 further comprising milling the exterior surface of the workpiece to refine the shape.

3. The method of claim 2 wherein milling the exterior surface of the workpiece includes moving a cutting tool through an arc to shape a computer-controlled location on the workpiece.

4. The method of claim 2 wherein milling the exterior surface of the workpiece includes moving a cutting tool through a translation in position to shape a computer-controlled location on the workpiece.

5. The method of claim 1 further comprising sintering the material on the stem.

6. The method of claim 1 further comprising curing the material on the stem by photopolymerization.

7. The method of claim 1 further comprising controlling a temperature of a region of the workpiece with a laser.

8. The method of claim 7 further comprising selectively directing two or more lasers at the workpiece.

9. The method of claim 1 further comprising controlling a temperature of the workpiece with a directed energy process including one or more of radiant heat and microwaves.

10. The method of claim 1 wherein depositing the material includes spraying the material in a powder form and heating the exterior surface of the workpiece with a laser where the material is to be applied to the workpiece.

11. A method comprising:
positioning a stem in a base;
affixing a coping to the base, the coping having an interior surface with a shape of a prepared surface for a dental restoration;
rotating the base; and
depositing a material on the coping under computer control to create a workpiece that includes the coping, the workpiece having a shape including an interior surface determined by the interior surface of the coping and an exterior surface determined by computer-controlled deposition of the material according to an exterior shape for the dental restoration.

12. The method of claim 11 further comprising milling the exterior surface of the workpiece to refine the shape.

13. The method of claim 12 wherein milling the exterior surface of the workpiece includes moving a cutting tool through an arc to shape a computer-controlled location on the workpiece.

14. The method of claim 12 wherein milling the exterior surface of the workpiece includes moving a cutting tool through a translation in position to shape a computer-controlled location on the workpiece.

15. The method of claim 11 further comprising sintering the material on the coping.

16. The method of claim 11 further comprising curing the material on the coping by photopolymerization.

17. The method of claim 11 further comprising controlling a temperature of a region of the workpiece with a laser.

18. The method of claim 17 further comprising selectively directing two or more lasers at the workpiece.

19. The method of claim 11 further comprising controlling a temperature of the workpiece with a directed energy process including one or more of radiant heat and microwaves.

20. The method of claim 11 wherein depositing the material includes spraying the material in a powder form and heating the exterior surface of the workpiece with a laser where the material is to be applied to the workpiece.

* * * * *